United States Patent
McFarland et al.

[11] Patent Number: 6,027,611
[45] Date of Patent: Feb. 22, 2000

[54] FACIAL TISSUE WITH REDUCED MOISTURE PENETRATION

[75] Inventors: Timothy Maurice McFarland, Neenah; Michael Francis Drymalski, Menasha; James Martin Kaun, Neenah; Marvin Edsel Swails, Appleton; Eric Francis Sweeney, Waupaca, all of Wis.

[73] Assignee: Kimberly-Clark Worldwide, Inc., Neenah, Wis.

[21] Appl. No.: 08/638,522

[22] Filed: Apr. 26, 1996

[51] Int. Cl.[7] .................................................. D21F 11/00
[52] U.S. Cl. ........................... 162/127; 162/123; 162/183; 162/164.1; 162/164.3; 162/158; 428/153
[58] Field of Search ..................................... 162/127, 123, 162/128, 158, 164.1, 164.3, 164.6, 112, 111, 168.3, 168.1, 183, 184; 428/153, 154, 211

[56] References Cited

U.S. PATENT DOCUMENTS

| | | | |
|---|---|---|---|
| Re. 29,960 | 4/1979 | Mazzerella et al. | 162/158 |
| 405,269 | 6/1889 | Menzies | 162/180 |
| 1,300,357 | 4/1919 | De Cew | 162/180 |
| 1,345,476 | 7/1920 | Clapp | 162/179 |
| 1,558,845 | 10/1925 | DeCew | 162/180 |
| 1,558,846 | 10/1925 | DeCew | 162/180 |
| 1,585,469 | 5/1926 | DeCew | 162/180 |
| 1,589,947 | 6/1926 | DeCew | 162/180 |
| 1,663,976 | 3/1928 | DeCew | 162/180 |
| 1,682,346 | 8/1928 | Lorenz | 162/112 |
| 1,753,775 | 4/1930 | DeCew | 162/180 |
| 1,799,216 | 4/1931 | DeCew | 162/180 |
| 1,836,455 | 12/1931 | Dreshfield | 162/180 |
| 1,839,449 | 1/1932 | Sutermiester et al. | 162/179 |
| 1,885,185 | 11/1932 | Curtis | 162/180 |
| 1,929,205 | 10/1933 | Libby | 92/91 |
| 2,041,285 | 5/1936 | DeCew | 92/91 |
| 2,186,709 | 1/1940 | Rowland | 92/91 |
| 2,197,383 | 4/1940 | Otterson | 92/91 |
| 2,546,705 | 3/1951 | Strawinski | 154/124 |

(List continued on next page.)

FOREIGN PATENT DOCUMENTS

| | | |
|---|---|---|
| 144658 | 6/1985 | European Pat. Off. . |
| 0 613 979 | 9/1994 | European Pat. Off. ........ D21F 11/14 |
| 588954 | 11/1933 | Germany . |
| 76/04923 | 6/1977 | South Africa . |
| 1504802 | 3/1978 | United Kingdom . |
| 2119709 | 11/1983 | United Kingdom . |
| 92/13713 | 8/1992 | WIPO . |
| 94/02681 | 2/1994 | WIPO . |
| 94/13883 | 6/1994 | WIPO . |

OTHER PUBLICATIONS

Patent Cooperation Treaty Search Report from the International Search Authority, International Application No. PCT/US 97/06028 dated Sep. 23, 1997.

*Primary Examiner*—Jose Fortuna
*Attorney, Agent, or Firm*—Gregory E. Croft

[57] ABSTRACT

Facial tissue is rendered resistant to water penetration while retaining softness by treating the fibers with a sizing agent prior to forming the sheet, or topically after the sheet is formed. The resulting tissue prevents the user's hands from becoming wetted during nose care.

10 Claims, 2 Drawing Sheets

U.S. PATENT DOCUMENTS

| | | | |
|---|---|---|---|
| 2,572,932 | 10/1951 | Horsey et al. | 92/91 |
| 2,684,300 | 7/1954 | Wilson et al. | 92/3 |
| 2,762,270 | 9/1956 | Keim et al. | 92/40 |
| 2,785,067 | 3/1957 | Osberg, Jr. | 92/21 |
| 2,897,108 | 7/1959 | Harwood | 154/50 |
| 2,897,109 | 7/1959 | Voigtman | 154/50 |
| 2,961,366 | 11/1960 | Weisgerber | 162/158 |
| 2,961,367 | 11/1960 | Weisgerber | 162/158 |
| 2,986,488 | 5/1961 | Weisgerber | 162/159 |
| 3,006,806 | 10/1961 | Schur | 162/158 |
| 3,212,961 | 10/1965 | Weisgerber | 162/158 |
| 3,311,532 | 3/1967 | Kulick et al. | 162/179 |
| 3,314,927 | 4/1967 | Worcester | 154/50 |
| 3,321,425 | 5/1967 | Blau et al. | 260/23 |
| 3,421,976 | 1/1969 | Jones | 162/180 |
| 3,470,055 | 9/1969 | Wade | 156/244 |
| 3,483,077 | 12/1969 | Aldrich | 162/158 |
| 3,536,563 | 10/1970 | Brandts et al. | 156/246 |
| 3,580,797 | 5/1971 | Asmuth | 161/126 |
| 3,613,142 | 10/1971 | Chaney | 15/104.94 |
| 3,669,822 | 6/1972 | Cowen | 161/130 |
| 3,684,643 | 8/1972 | Stepp | 161/160 |
| 3,862,877 | 1/1975 | Camden | 161/57 |
| 3,950,578 | 4/1976 | Laumann | 427/378 |
| 4,166,001 | 8/1979 | Dunning et al. | 162/111 |
| 4,178,407 | 12/1979 | Rubens | 428/284 |
| 4,214,948 | 7/1980 | Mazzarella et al. | 162/158 |
| 4,222,820 | 9/1980 | Hiskens et al. | 162/158 |
| 4,243,481 | 1/1981 | Dumas | 162/158 |
| 4,295,931 | 10/1981 | Dumas | 162/158 |
| 4,302,283 | 11/1981 | Blitzer et al. | 162/158 |
| 4,405,408 | 9/1983 | Yoshioka et al. | 162/158 |
| 4,407,994 | 10/1983 | Bankert et al. | 524/107 |
| 4,431,826 | 2/1984 | Sweeney | 549/255 |
| 4,434,269 | 2/1984 | Probst et al. | 524/538 |
| 4,478,682 | 10/1984 | Bankert et al. | 162/158 |
| 4,481,243 | 11/1984 | Allen | 428/154 |
| 4,489,118 | 12/1984 | Endres et al. | 428/154 |
| 4,505,754 | 3/1985 | Gowan, Jr. | 106/238 |
| 4,522,686 | 6/1985 | Dumas | 162/158 |
| 4,529,477 | 7/1985 | Okada et al. | 106/287.23 |
| 4,544,414 | 10/1985 | Kawatani et al. | 106/287.24 |
| 4,545,855 | 10/1985 | Sweeney | 162/159 |
| 4,545,856 | 10/1985 | Sweeney | 162/158 |
| 4,574,021 | 3/1986 | Endres et al. | 428/154 |
| 4,606,773 | 8/1986 | Novak | 106/213 |
| 4,648,876 | 3/1987 | Becker et al. | 604/370 |
| 4,657,538 | 4/1987 | Becker et al. | 604/381 |
| 4,657,946 | 4/1987 | Rende et al. | 523/402 |
| 4,673,439 | 6/1987 | Takahashi et al. | 106/287.24 |
| 4,687,519 | 8/1987 | Trzasko et al. | 106/211 |
| 4,695,401 | 9/1987 | Sweeney | 252/312 |
| 4,711,671 | 12/1987 | Mazzarella et al. | 106/243 |
| 4,721,655 | 1/1988 | Trzasko et al. | 428/530 |
| 4,728,366 | 3/1988 | Mazzarella et al. | 106/243 |
| 4,737,239 | 4/1988 | Bernheim et al. | 162/158 |
| 4,747,910 | 5/1988 | Mazarella et al. | 162/158 |
| 4,816,320 | 3/1989 | St. Cyr | 428/198 |
| 4,832,792 | 5/1989 | Mazzarella et al. | 162/158 |
| 4,849,055 | 7/1989 | Yoshioka et al. | 162/158 |
| 4,859,720 | 8/1989 | Flesher et al. | 523/158 |
| 4,915,726 | 4/1990 | Sweeney | 162/158 |
| 4,919,725 | 4/1990 | Jones | 106/218 |
| 5,104,486 | 4/1992 | Sweeney | 162/158 |
| 5,114,538 | 5/1992 | Malatesta et al. | 162/158 |
| 5,176,748 | 1/1993 | Nikoloff et al. | 106/211 |
| 5,196,244 | 3/1993 | Beck | 428/35.2 |
| 5,224,993 | 7/1993 | Takahashi et al. | 196/287.2 |
| 5,252,754 | 10/1993 | Bottorff | 549/328 |
| 5,397,435 | 3/1995 | Ostendorf et al. | 162/112 |
| 5,397,436 | 3/1995 | Robeson et al. | 162/158 |
| 5,399,412 | 3/1995 | Sudall et al. | 428/153 |
| 5,407,537 | 4/1995 | Malatesta et al. | 162/158 |
| 5,437,766 | 8/1995 | Van Phan et al. | 162/127 |
| 5,472,485 | 12/1995 | Pandian et al. | 106/194 |
| 5,494,554 | 2/1996 | Edwards et al. | 162/111 |

FACIAL TISSUE WITH REDUCED MOISTURE PENETRATION

BACKGROUND OF THE INVENTION

Although facial tissues have a large number of uses, nose care (wiping and blowing) is the primary use (about 70–80% of all usage occasions). To this end, softness has always been a significant tissue property in order to prevent irritation of the skin. Accordingly, the tissue industry has continually sought to increase softness. However, a property of soft tissues that has not been addressed in commercially available tissues is wet-through during nose care. Wet-through is not only undesirable from an aesthetic and cleanliness standpoint, it is also known that some viruses, such as cold viruses, can be spread when nasal discharge contacts the user's hands.

In order to combat wet-through, some consumers use multiple tissues to increase the effective absorbent capacity to capture as much of the mucus as possible. However, this is not always practical or effective.

Hence, there is a need for a soft tissue, particularly facial tissue, that prevents or substantially inhibits nasal discharge wet-through during nose blowing.

SUMMARY OF THE INVENTION

It has now been discovered that facial tissues can be made to substantially eliminate moisture penetration without deleteriously affecting the softness or increasing the stiffness of the tissue by adding one or more sizing agents to the papermaking fibers prior to forming the tissue or topically to the surface of the formed sheet.

Hence, in one aspect, the invention resides in a facial tissue comprising cellulosic papermaking fibers to which a sizing agent has been added, said tissue having an Absorbency Rate (hereinafter defined) of about 10 seconds or greater and an MD Modulus (hereinafter defined) of about 30 kilograms or less. The Absorbency Rate is a measure of the water penetration resistance imparted to the tissue, while the MD Modulus is a measure of the softness or stiffness of the tissue. The tissues of this invention are remarkably water repellent, yet still soft.

In another aspect, the invention resides in a method of making a tissue comprising: a) forming a first aqueous suspension comprising papermaking fibers and a sizing agent; b) forming a second aqueous suspension comprising papermaking fibers; c) separately feeding the first and second aqueous suspensions to a layered headbox; d) depositing the first and second aqueous suspensions onto a forming fabric to form a layered web, wherein the first suspension is deposited between the second suspension and the forming fabric; and e) drying the web to form a tissue sheet.

As used herein, a "sizing agent" is any chemical that imparts water repellency to cellulosic fibers. Suitable sizing agents are disclosed in a text entitled "Papermaking and Paper Board Making," second edition, Volume III, edited by R. G. MacDonald, and J. N. Franklin, which is herein incorporated by reference.

Sizing agents are commonly added to control the penetration of aqueous liquids into paper or other fibrous structures. In many cases, a certain resistance is required for end use. When surface treatments are applied with conventional equipment often sizing is required in the base sheet to control pickup of the aqueous solution. Paper grades such as butcher's wrap, milk carton, linerboard, bleached and unbleached bag, fine paper, cylinder board, newsprint and corrugated medium are routinely sized.

Internal sizing agents, which are those applied to the fibers within the paper structure, provide a reduced rate of penetration by retarding the rate of flow through the inter-fiber capillaries. When sizing is accomplished, the contact angle at the fiber surface is 90 degrees or greater. Internal sizing agents function through the use of low surface energy, hydrophobic chemicals which when attached to the surface of cellulose reduce the surface energy of the fiber surface.

Particularly suitable sizing agents are acid or alkaline sizes such as acid rosin, alkenyl ketene dimers, alkenyl succinic anhydride, alkyl ketene dimers and alkenol ketene dimers of the formula:

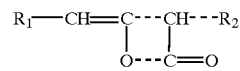

wherein $R_1$ and $R_2$ are based on $C_{16}$–$C_{18}$, aliphatic carbon chains, which can be the same or different. Exemplary commercially available sizing agents of this type are Hercon 79 and Precis 3000 from Hercules, Inc., Wilmington, Del. The amount of the sizing agent added to the fibers can be from about 1 to about 10 pounds per ton of fiber, more specifically from about 1.5 to about 3 pounds per ton of fiber, and still more specifically, from about 2 to about 2.5 pounds per ton of fiber.

As used herein, the "Absorbency Rate" is a measure of the water repellency imparted to the tissue by the sizing agent. The Absorbency Rate is the time it takes for a product to be thoroughly saturated in distilled water. To measure the Absorbency Rate, samples are prepared as 2½ inch squares composed of 20 finished product sheets using a die press (e.g. TMI DGD from Testing Machines Incorporated Inc., Amityville, N.Y. 11701). The ply of a finished product dictates the number of individual sheets: 1-ply: 20 individual sheets; 2-ply: 40 individual sheets; 3-ply: 60 individual sheets. When testing soft rolls (single ply of tissue coming off the tissue machine before plying at the rewinder), 40 individual softroll sheets are used per sample (if the intended finished product is 2-ply.)

The samples are stapled in all four corners using Swingline S.F 4 inch speedpoint staples. Samples are tested in a constant temperature water bath at a depth of at least 4 inches (maintained through out testing) containing distilled water at 30+/–1° Celsius. The sample is held approximately one inch above the water surface (staple points in the down position) and then dropped flat on the water surface. A stopwatch (readable to 0.1 seconds) is started when the sample hits the water. When the sample is completely saturated the stop watch is stopped and the Absorbency Rate is recorded. A minimum of five samples are tested and the test results are averaged. All tests are conducted in a laboratory atmosphere of 23+/–1° Celsius and 50+/–2% RH. All samples are stored under these conditions for at least 4 hours before testing. (Sizing agents distribute themselves and react faster at higher temperatures.)

The tissues of this invention have an Absorbency Rate of about 10 seconds or greater, more specifically about 100 seconds or greater, still more specifically about 200 seconds or greater, still more specifically about 300 seconds or greater, and still more specifically from about 100 to about 400 seconds.

The "MD Modulus" is a measure of the softness of the tissue sheet and is the slope of the least squares straight line between the 70 and 157 gram points for the load vs. the percent elongation of the sample. MD Modulus values are obtained using conventional tensile testing instruments e.g., Sintech/2 Computer integrated testing system. A single facial tissue is cut to a 3 inch width with a die cutter. The test sample length should exceed the gage length (distance between the jaws of the tensile tester) by at least two inches. The test sample should not have any tears or creases and should have clean cut and parallel edges. The tensile tester jaws are opened and the test specimen is placed between the jaws; straight and centered. The jaws are closed on the specimen and the testing protocol is initiated. The specimen is pulled at $\frac{1}{3}$ normal test speed (ten inches per minute). When the test load reaches 0.5% of the full scale load, the elongation is measured to correct for any slack in the test specimen. At that point the crosshead changes speed and continues at the normal test speed. Data is collected until the peak load is reached and the load drops to 65% of the peak load. A suitable tensile tester can be obtained from Sintech Inc., P.O. Box 14226, Research Triangle Park N.C. 27709-4226.

The tissues of this invention can have an MD Modulus of about 30 kilograms or less, more specifically about 20 kilograms or less, still more specifically about 10 kilograms or less, and still more specifically about 5 kilograms or less, and still more specifically from about 3 to about 10 kilograms.

A further characteristic of the tissues of this invention, as well as typical facial tissues, is a high degree of "Porosity" which is not greatly reduced, if at all, by the sizing agent, which treats the individual fibers but does not clog the pore structure. The Porosity is determined by a test that measures the air permeability of fabrics in terms of cubic feet of air per square foot of sheet using a Textest FX3300 air permeability tester manufactured by Textest Ltd., Zurich, Switzerland. All tests are conducted in a laboratory with a temperature of 23+/-2° C. and 50+/-5% RH. Specifically, a single sheet of facial tissue is clamped over the 2.75-inch diameter fabric test opening. Placing folds or crimps above the fabric test opening is to be avoided if at all possible. The unit is turned on, the Powerstat is slowly turned clockwise until the inclined manometer oil column reaches 0.5. Once the inclined manometer oil level has steadied at 0.5, the level of oil in the vertical manometer is recorded. The vertical manometer reading is converted to a flow rate in units of cubic feet of air per minute per square foot of sample.

The 2-ply tissues of this invention can have a Porosity of about 50 cubic feet per minute or greater, more specifically about 70 cubic feet per minute or greater, and still more specifically from about 60 to about 90 cubic feet per minute.

The "caliper" (thickness) of facial tissues is tested with an EMVECO Model 200-A instrument. This instrument has a motor driven dead weight, LCD (digital) micrometer. The instrument measures thickness by lowering a pressure foot at approximately 0.8 mm/s onto the tissue sheet which lays on an anvil. The anvil has the same surface area as the pressure foot. The anvil is also parallel to the pressure foot. Tests are conducted at a temperature of 23+/-1° C. and 50+/-2% RH. The instrument should be started and zeroed according the manufacturer's instructions. The tissue is then placed on the anvil so that the pressure foot is at least ¼ inch away from the edges and/or crimp marks of the specimen. The pressure foot will lower down onto the tissue and a caliper reading will appear on the instrument. Two readings should be taken per specimen from diagonal corners, within six inches of each other in the CD direction. The average of the two readings is recorded.

Sheet "bulk" is calculated by dividing the caliper (mm) by the basis weight (g/m$^2$) of the sheet.

"Density" is the inverse of the bulk. The density of the tissues of this invention can be about 0.25 gram per cubic centimeter or less, more specifically about 0.2 gram per cubic centimeter or less, and still more specifically from about 0.2 to about 0.1 gram per cubic centimeter.

The basis weight of the tissues of this invention can be from about 5 to about 70 grams per square meter, more specifically from about 10 to about 40 grams per square meter, and still more specifically from about 20 to about 30 grams per square meter.

The tissues of this invention can also be characterized by a geometric mean tensile strength of from about 500 to about 900 kilograms, more specifically from about 600 to about 800 kilograms. Geometric mean tensile strength is the square root of the MD tensile peak load times the CD tensile peak load.

DETAILED DESCRIPTION OF THE DRAWINGS

Figure 1:
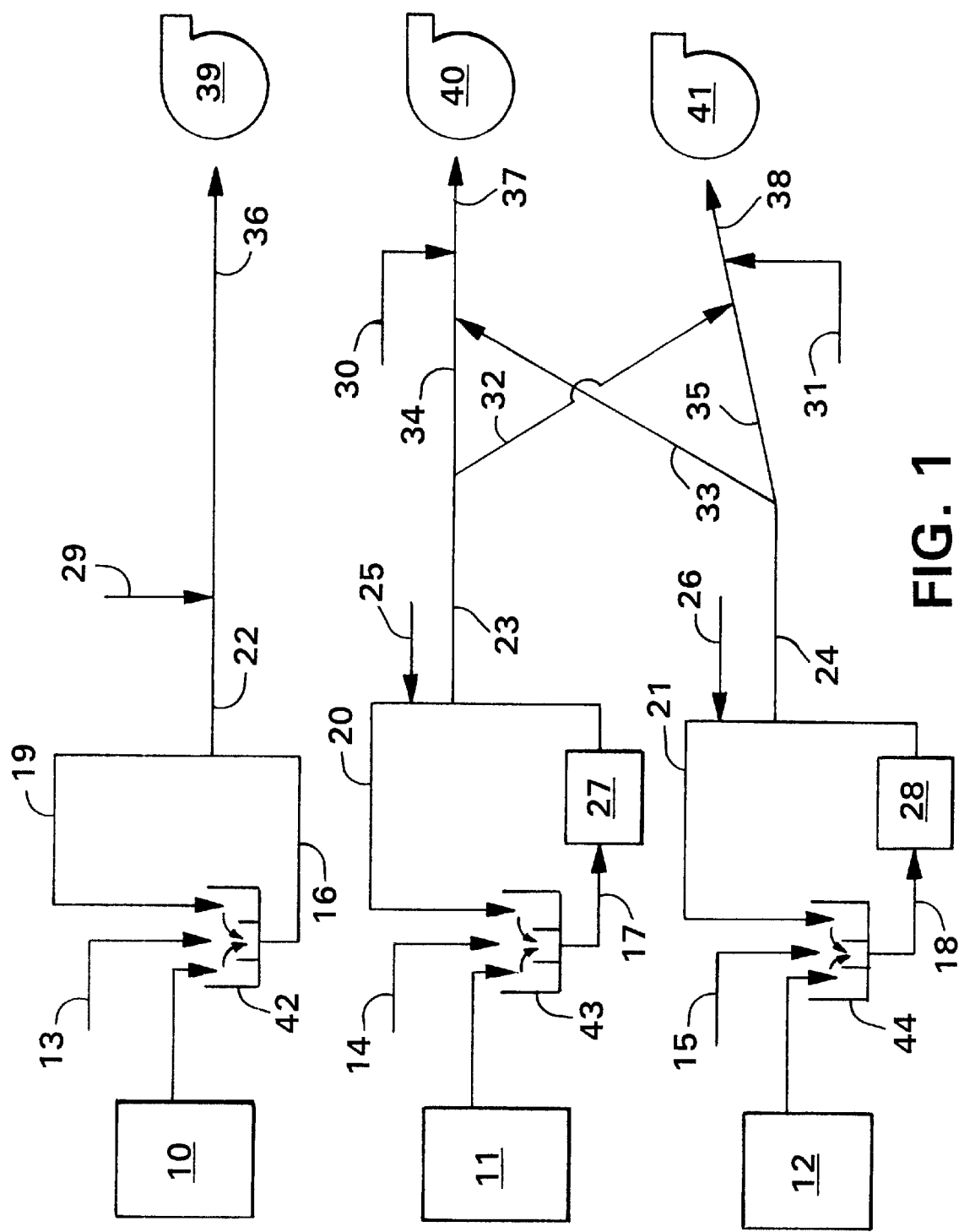
FIG. 1 is a schematic flow diagram of a wet-end stock system useful for purposes of this invention.

FIG. 1 illustrates a wet-end stock system which could be used in the manufacture of sized tissue. Shown is a split stock system with 3 chests 10,11,12 for the storage of an aqueous suspension of papermaking fibers. From these chests, the fiber-water suspensions enter 3 separate stuffboxes 42,43,44 used to maintain a constant pressure head. A split stock system has the advantage of being able to selectively apply chemicals to certain fibers and to layer these fibers during the forming process. Alternatively, a single stream stock system can be used with 1 chest, 1 stuffbox, and 1 fan pump.

A portion of the outlet stream 16 of stuffbox 42 can be drawn off as a separate stream 22 and sent to a fan pump 39 while the remaining portion 19 can be recirculated back to the top of the stuff box. Alternatively, the entire outlet of the stuffbox can be sent to the fan pump 39. Sizing agents can be added at any point between chest 10 and the headbox 62 shown in FIG. 2, addition points 13 and 29 for example. The optimal sizing agent addition point is specific to the type of sizing agent used. Alternatively, no sizing agent can be added to these fibers.

A portion of the outlet stream 17 of stuffbox 43 can be drawn off as a separate stream 23 while the remaining portion 20 can be recirculated to the top of the stuffbox. Alternatively, the entire outlet of the stuffbox can be drawn off as stream 23. Stream 23 is subsequently split into streams 33 and 35. Sizing agents can be added at any point between chest 11 and streams 32 and 34; addition points 14 and 25 are given for example.

A portion of the outlet stream 18 of stuffbox 44 can be drawn off as a separate stream 24 while the remaining portion 21 can be recirculated to the top of the stuffbox. Alternatively, the entire outlet of the stuffbox can be drawn off as stream 24. Stream 24 is subsequently split into streams 33 and 35. Sizing agents can be added at any point between chest 12 and streams 33 and 35; addition points 15 and 26 are given for example.

Streams 33 and 34 can then be combined to form stream 37 and streams 32 and 35 can then be combined to form stream 38. Sizing agents can also be added to streams 37 and 38. Alternatively, streams 23 and 24 can remain unsplit and become streams 37 and 38 respectively. Although not shown in FIG. 1, streams 22,23, and 24 can each be split into 3 separate streams and recombined such that a mixture of fibers from each stream 22, 23 and 24 goes to each fan pump 39, 40, and 41.

Other functional chemicals such as dry strength resins and wet strength resins can also be added anywhere between chests 10, 11, 12 and headbox 62. Additionally, the stock can be passed through refiners, 27 and 28 are shown for example.

Figure 2:
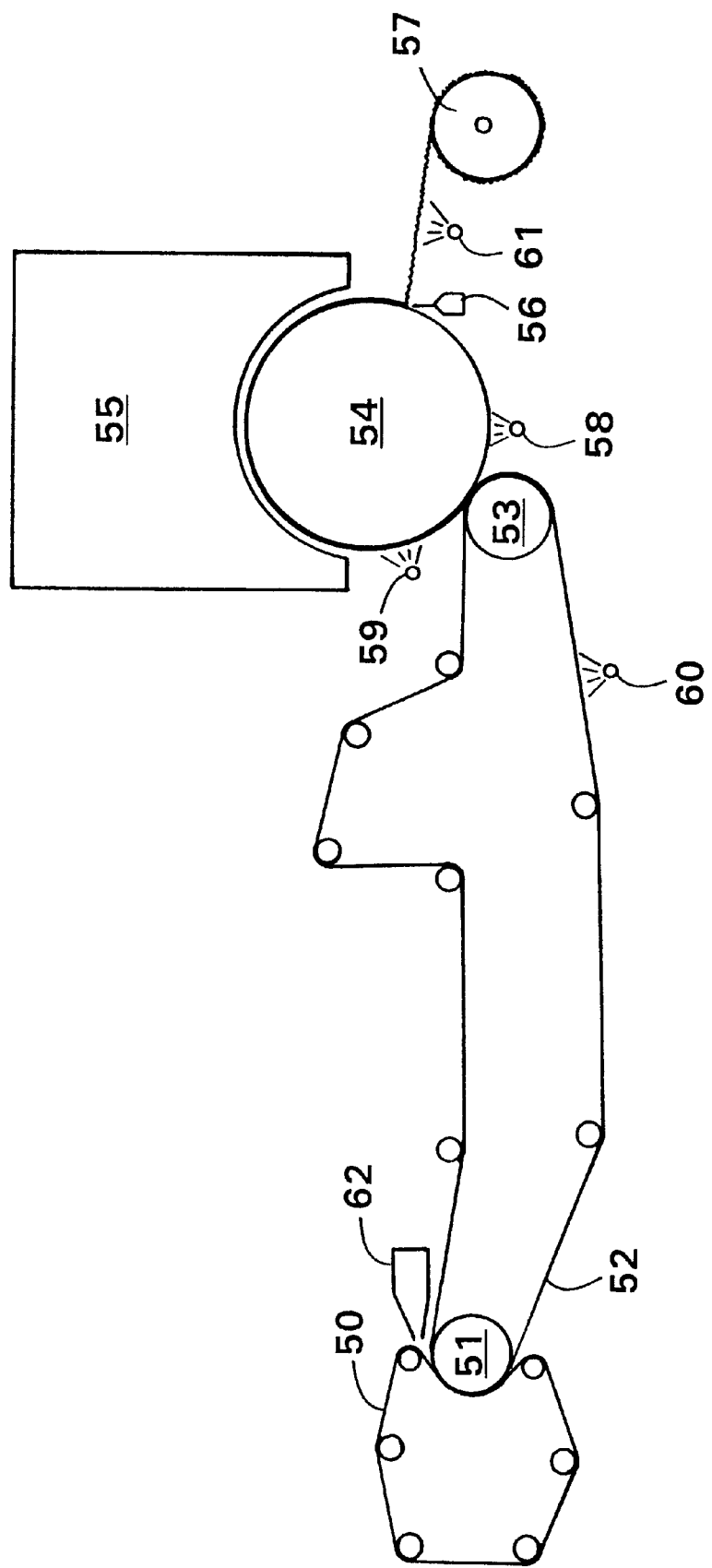
FIG. 2 is a schematic flow diagram of a tissue making process in accordance with this invention.

FIG. 2 is a schematic of the process flow diagram illustrating the machine used to manufacture sized tissue sheets. Shown is a crescent former having a layered papermaking headbox 62 which continuously injects or deposits a layered stream of an aqueous suspension of papermaking fibers between a forming fabric 50 and a press felt 52, which is partially wrapped around the form roll 51. Water is removed from the aqueous stock suspension through the forming fabric by centrifugal force as the newly formed web traverses the arc of the form roll. The wet web is dewatered to a consistency of about 12 dry weight percent prior to the vacuum pressure roll 53. The multilayer headbox 62 is supplied by three fan pumps 39, 40 and 41 as shown in FIG. 1. The fan pumps can supply the same fiber types to all three headbox layers or can supply different fiber types to each layer. Similarly, one large fan pump can supply a monolayer headbox which delivers a blend of papermaking fibers. The upper layer or dryer layer of the multilayer headbox can supply, by way of example, eucalyptus fibers from the dryer layer fan pump 39. This layer can make up 40 to 70 dry weight percent of the overall web furnish. The middle and bottom layers can be supplied with softwood and hardwood via the middle and felt layer fan pumps 40 & 41 respectively to form a strong papermaking fiber layer within the tissue web. Papermaking fibers treated with sizing agent can be supplied to any combination of or all three headbox layers.

After the forming fabric and press felt separate, the wet web is transported on the press felt to the vacuum pressure roll 53 where it is pressed against the yankee dryer 54 with an application force of about 200 pounds per square inch and further dewatered to about 42 dry weight percent. Alternatively, sizing agent can be sprayed onto the moving tissue web via a spray boom 60 located prior to the pressure roll or via a spray boom 59 after the tissue web has transferred to the yankee dryer.

The steam heated yankee dryer 54 and gas fired high temperature air hood 55 dry the tissue web to a dry weight consistency of 96% or higher. The temperature of the tissue web when it reaches the creping doctor blade 56, as measured by an infra-red temperature sensor, is about 200° F. or greater, preferably 220° F. or greater, and more preferably about 235° F. These high temperatures aid in the curing of the sizing agent.

An aqueous adhesive mixture is sprayed continuously onto the yankee dryer via a spray boom 58 which evenly sprays the adhesive onto the dryer surface. The point of application onto the dryer surface is between the creping doctor blade 56 and vacuum pressure roll. The adhesive mixture aids in the adhesion of the web to the yankee dryer and thereby enhances the crepe performance when the sheet is removed from the dryer via a creping doctor blade. The creped tissue is wound onto a core 57 in the reel section which runs at a speed about 30% slower than the yankee dryer. Sizing agent can be applied to the dry web by spraying an aqueous solution through a spray boom 61 located between the creping doctor 56 and the winding tissue roll 57. Similarly, sizing agents can be sprayed in off-line rewinder operations by using similar a similar spray boom or by other off-line application methods used in papermaking.

EXAMPLES

Example 1.

To illustrate the invention, facial tissue wadding was produced on an experimental tissue machine similar to that illustrated in FIGS. 1 and 2. Eucalyptus fibers were pulped for 30 minutes and placed in a holding chest which fed into chest 10. Likewise a mixture of 72% Northern Softwood Kraft and 28% Northern Hardwood Kraft was pulped for 30 minutes and placed in a holding chest which fed into chests 11 and 12. The eucalyptus fiber entered stuffbox 42 and exited through stream 16. A portion of stream 16 was drawn off to form stream 22, which became stream 36 and entered fan pump 39, the dryer layer fan pump. No chemical addition was made to this stream.

The Northern Softwood/Northern Hardwood Kraft fiber mixture (hereafter referred to as the LL19/LL16 fibers) in chest 11 were fed to stuffbox 43. The outlet stream 17 fed refiner 27 operating at no load setpoint to minimize the refining action. A portion of stream 17 was drawn off (approximately 30% of stream 17) to form stream 23. A commercially available wet strength chemical was added at point 25 in the amount of 0.82 lbs/ton of active solids per total sheet weight. Stream 23 was then split with 50% going to stream 32 and 50% going to form stream 34.

The LL19/LL16 fibers in chest 12 were fed to stuffbox 44. The sizing agent (Hercon 79, commercially available from Hercules Incorporated) was fed into the stuffbox outlet via chemical addition point 15 at an addition rate of 1.25 lbs/ton of active solids per total sheet weight. The refiner 28 shown in FIG. 1 was bypassed. A portion of stream 18 was drawn off (approximately 30% of stream 18) to form stream 24. A commercially available wet-strength agent was added at point 26 in the amount of 0.82 lbs/ton of active solids per total sheet weight. Stream 24 was then split with 50% going to form stream 33 and 50% going to from stream 35.

Streams 32 and 35 were then combined to form stream 38 which fed fan pump 41, the felt layer fan pump. A commercially available chemical was added at points 30 and 31 for the purpose of controlling finished dry tensile strength. Streams 33 and 34 were combined to form stream 37 which fed fan pump 40, the middle layer fan pump. A commercially available chemical was added at point 30 for the purpose of controlling finished dry tensile strength. Therefore, both streams 37 and 38 were compromised entirely of the LL19/LL16 fiber, half having been refined and the other half having a sizing agent added to.

The eucalyptus fiber suspension from fanpump 39 was fed to the upper layer/dryer layer of headbox 62 (in FIG. 2) at 0.1% consistency (lbs dry fiber/lb total*100%). An amount of eucalyptus fiber was added to fanpump 39 such that 50% of the total finished sheet weight was eucalyptus. The LL19/LL16 fibers from fanpumps 40 and 41 fed the middle layer and lower layer/felt layer of headbox 62 at 0.05% consistency. An amount of LL19/LL16 fiber was added such that 25% of the total finished weight was LL1 9/LL1 6 from fanpump 40 and 25% was from fanpump 41.

The multilayer headbox 62 injected this aqueous suspension of papermaking fiber between an Appleton Mills 2164A forming fabric 50 and Appleton Mills style 5611-AmFlex 2 S press felt 52. The felt and fabric were traveling at 3000 ft/min and the headbox jet velocity was adjusted to reach the desired ratio of MD tensile to CD tensile, typically 2850 ft/min. Water was removed from the deposited papermaking slurry through the forming fabric due to centrifugal force as the newly formed wet web traversed the arc of forming roll 51. Upon the separation of the forming fabric and press felt, the wet-web, dewatered to about 12% consistency, was transported on the press felt 52 to the vacuum pressure roll 53. The rubber covered vacuum pressure roll further dewatered the wet web to approximately 42% consistency via mechanical pressing against the Yankee dryer 54 at 200 psi nip pressure with 5" vacuum pressure across the press felt.

The steam heated yankee dryer 54 and gas fired high temperature air hood 55 dried the tissue web to a dry weight consistency greater than 96%. Prior to sheet removal from the dryer via creping doctor blade 56, the sheet temperature reached in excess of 180 degrees F. An aqueous mixture of adhesive was continuously sprayed onto the yankee dryer via spray boom 58. The creped web was then wound onto a core 57 running at a speed approximately 30% slower than the yankee dryer.

The final sheet had the following fiber composition: 50% Eucalyptus (EUC), 36% northern softwood kraft (LL19), and 14% northern hardwood kraft (LL16).

| LAYER | FURNISH | STOCK SPLIT | TREATMENT | BASIS WEIGHT |
|---|---|---|---|---|
| DRYER | EUC | 50% | none | 3.6 |
| MID | LL19/ LL16 | 25% | ½ refined & ½ sized | 1.8 |
| FELT | LL19/ LL16 | 25% | ½ refined & ½ sized | 1.8 |
| | | | Total: | 7.2 lbs/2880 ft² |

The Absorbency Rate of Example 1 was tested at least 15 days after manufacture of the basesheet. The Absorbency Rate of Example 1 was 14 seconds. Other product data is given in Table 1.

Example 2

Example 2 was produced in a manner identical to Example 1, but with Hercon 79 added at 1.5 lb/ton of active solids per total sheet weight via chemical addition point 15.

The Absorbency Rate of Example 2 was tested at least 15 days after manufacture of the basesheet. The absorbency rate of Example 2 was 24 seconds. Other product data is given in Table 1.

Example 3

Example 3 was produced in a manner identical to Example 1, but with Hercon 79 added at 1.75 lb/ton of active solids per total sheet weight via chemical addition point 15.

The Absorbency Rate of Example 3 was tested at least 15 days after manufacture of the basesheet. The Absorbency Rate of Example 3 was 41 seconds. Other product data is given in Table 1.

Example 4

Example 4 was produced in a manner identical to Example 1, but with no Hercon 79 added to act as a control to compare with Examples 1–3.

The Absorbency Rate of Example 4 was tested at least 15 days after manufacture of the basesheet. The Absorbency Rate of Example 4 was 2.7 seconds. Other product data is given in Table 1.

Example 5

Example 5 was produced in a manner identical to Example 1, but with an alternate sizing agent, Precis 3000 (available from Hercules Incorporated) added at 1 lb/ton of active solids per total sheet weight via chemical addition point 15.

The Absorbency Rate of Example 5 was tested at least 15 days after manufacture of the basesheet. The Absorbency Rate of Example 5 was 17 seconds. Other product data is given in Table 1.

Example 6

Example 6 was produced in a manner identical to Example 1, but with Precis 3000 added at 1.25 lb/ton of active solids per total sheet weight via chemical addition point 15.

The Absorbency Rate of Example 6 was tested at least 15 days after manufacture of the basesheet. The Absorbency Rate of Example 6 was 36 seconds. Other product data is given in Table 1.

Example 7

Example 7 was produced in a manner identical to Example 1, but with Precis 3000 added at 1.5 lb/ton of active solids per total sheet weight via chemical addition point 15.

The Absorbency Rate of Example 7 was tested at least 15 days after manufacture of the basesheet. The Absorbency Rate of Example 7 was 105 seconds. Other product data is given in Table 1.

Example 8

Example 8 was produced in a manner identical to Example 1, but with Precis 3000 added at 1.75 lb/ton of active solids per total sheet weight via chemical addition point 15.

The Absorbency Rate of Example 8 was tested at least 15 days after manufacture of the basesheet. The Absorbency Rate of Example 1 was 325 seconds. Other product data is given in Table 1.

Example 9

Example 9 was produced in a manner identical to Example 1, but with Precis 3000 added at 1.5 lb/ton of active solids per total sheet weight via chemical addition point 15.

The Absorbency Rate of Example 9 was tested at least 15 days after manufacture of the basesheet. The Absorbency Rate of Example 9 was 3 seconds. Other product data is given in Table 1.

TABLE 1

|  | No. of tests | Example 1 | Example 2 | Example 3 | Example 4 |
|---|---|---|---|---|---|
| Sizing Agent |  | Hercon 79 | Hercon 79 | Hercon 79 | None |
| Sizing Agent Dosage (lb/MT) |  | 1.25 | 1.5 | 1.75 | 0 |
| Absorbency Rate (sec) | 5 | 14 | 24 | 41 | 2.7 |
| Basis Weight (grams/sq meter) | 2 | 30.54 | 30.44 | 29.86 | 29.95 |
| Bulk (cm3/gm) |  | 8.07 | 8.01 | 8.08 | 8.38 |
| Porosity (ft3/min) | 5 | 70.56 | 70.68 | 69.5 | 76.4 |
| MD Tensile (gm/3 in) | 10 | 933 | 939 | 926 | 903 |
| CD Tensile (g/m3 in) | 10 | 458 | 475 | 475 | 475 |
| MD Slope (kg/3 in) | 10 | 4.534 | 4.378 | 4.713 | 4.396 |
| CD Slope (kg/3 in) | 10 | 14.467 | 15.226 | 15.249 | 15.391 |

|  | No. of tests | Example 5 | Example 6 | Example 7 | Example 8 | Example 9 |
|---|---|---|---|---|---|---|
| Sizing Agent |  | Precis 3000 | Precis 3000 | Precis 3000 | Precis 3000 | None |
| Sizing Agent Dosage (lb/MT) |  | 1 | 1.25 | 1.5 | 1.75 | 0 |
| Absorbency Rate (sec) | 5 | 17 | 36 | 105 | 325 | 3 |
| Basis Weight (grams/sq meter) | 2 | 30.97 | 30.44 | 31.78 | 31.11 | 30.3 |
| Bulk (cm3/gm) |  | 8.53 | 8.59 | 8.63 | 8.16 | 8.55 |
| Porosity (ft3/min) | 5 | 78.82 | 79.86 | 77.58 | 75.46 | 76.08 |
| MD Tensile (gm/3 in) | 10 | 759 | 867 | 847 | 930 | 855 |
| CD Tensile (gm/3 in) | 10 | 458 | 448 | 459 | 464 | 455 |
| MD Slope (Kg) | 10 | 3.678 | 3.796 | 3.688 | 4.264 | 3.723 |
| CD Slope (Kg) | 10 | 14.736 | 14.692 | 14.501 | 14.587 | 15.065 |

It will be appreciated that the foregoing examples, given for purposes of illustration, are not to be construed as limiting the scope of this invention, which is defined by the following claims and all equivalents thereto.

What is claimed is:

1. A method of making a soft tissue comprising:

a) forming a first aqueous suspension comprising papermaking fibers and a sizing agent;

b) forming a second aqueous suspension of papermaking fibers;

c) separately feeding the first and second aqueous suspensions to a layered headbox;

d) depositing the first and second aqueous suspensions onto a forming fabric to form a layered web wherein the first suspension is deposited between the second suspension and the forming fabric; and e) drying the web to form a tissue sheet.

2. The method of claim 1 wherein the sizing agent is selected from the group consisting of acid rosin, alkyl ketene dimers, alkenyl ketene dimers, alkenyl succinic anhydride and combinations thereof.

3. The method of claim 1 wherein the amount of the sizing agent added is from about 0.25 to about 10 dry pounds of active size per ton of sized papermaking fiber.

4. The method of claim 1 wherein the amount of the sizing agent added is from about 1 to about 6 dry pounds of active size per ton of sized papermaking fiber.

5. The method of claim 1 wherein the amount of sizing agent added is from about 2 to about 4 dry pounds of active size per ton of sized papermaking fiber.

6. A method for making soft tissue comprising:

a) forming a first aqueous suspension comprising papermaking fibers and a sizing agent;

b) forming a second aqueous suspension comprising papermaking fibers and a sizing agent;

c) forming a third aqueous suspension comprising papermaking fibers and a sizing agent;

d) separately feeding the three aqueous suspensions to a layered headbox;

e) depositing the three aqueous suspensions onto a forming fabric to form a layered web; and f) drying the web to form a tissue sheet.

7. The method of claim 6 wherein the sizing agent is selected from the group consisting of acid rosin, alkyl ketene dimers, alkenyl ketene dimers, alkenyl succinic anhydride and combinations thereof.

8. The method of claim 6 wherein the amount of the sizing agent added is from about 0.25 to about 10 dry pounds of active size per ton of sized papermaking fiber.

9. The method of claim 6 wherein the amount of the sizing agent added is from about 1 to about 6 dry pounds of active size per ton of sized papermaking fiber.

10. The method of claim 6 wherein the amount of sizing agent added is from about 2 to about 4 dry pounds of active size per ton of sized papermaking fiber.

* * * * *